(12) United States Patent
Hogset et al.

(10) Patent No.: US 10,166,401 B2
(45) Date of Patent: Jan. 1, 2019

(54) ANTIGEN DELIVERY DEVICE AND METHOD

(71) Applicant: PCI Biotech AS, Lysaker (NO)

(72) Inventors: Anders Hogset, Oslo (NO); Per Edvard Walday, Oslo (NO); Kristin Eivindvik, Fornebu (NO)

(73) Assignee: PCI BIOTECH AS, Oslo (NO)

( * ) Notice: Subject to any disclaimer, the term of this patent is extended or adjusted under 35 U.S.C. 154(b) by 112 days.

(21) Appl. No.: 14/914,985

(22) PCT Filed: Aug. 28, 2014

(86) PCT No.: PCT/EP2014/068236
§ 371 (c)(1),
(2) Date: Feb. 26, 2016

(87) PCT Pub. No.: WO2015/028541
PCT Pub. Date: Mar. 5, 2015

(65) Prior Publication Data
US 2016/0199664 A1    Jul. 14, 2016

(30) Foreign Application Priority Data
Aug. 28, 2013 (GB) .................................. 1315288.9

(51) Int. Cl.
*A61M 1/30* (2006.01)
*A61N 5/06* (2006.01)
(Continued)

(52) U.S. Cl.
CPC .......... *A61N 5/062* (2013.01); *A61M 37/0015* (2013.01); *A61B 2017/00172* (2013.01);
(Continued)

(58) Field of Classification Search
CPC .. A61K 41/0057; A61K 9/0021; A61K 9/703; A61K 9/7084; A61N 2005/0645;
(Continued)

(56) References Cited

U.S. PATENT DOCUMENTS

| 5,474,528 A | 12/1995 | Meserol |
| 5,705,518 A | 1/1998 | Richter et al. |

(Continued)

FOREIGN PATENT DOCUMENTS

| DE | 10 2008 010 890 | 8/2009 |
| WO | 95/25563 | 9/1995 |

(Continued)

OTHER PUBLICATIONS

Waeckerle-Men et al., Photochemical Targeting of Antigens to the Cytosol for Stimulation of MHC Class-I-Restricted T-Cell Responses, Eur. J. Pharma. Biopharma 85(1): 34-41 (2013).

(Continued)

*Primary Examiner* — Rebecca E Eisenberg
(74) *Attorney, Agent, or Firm* — Wedneroth, Lind & Ponack, L.L.P.

(57) ABSTRACT

A device for activating light-induced rupture of endocytic vesicles in target cells of a patient so as to effect delivery of an administered antigen to cytosol in the target cells, is described. The device is adapted to be worn by a patient over a region of skin where an antigen and a photosensitising agent are to be administered. The device comprises a rear surface that is rounded or otherwise configured to be worn against the patient's skin. It has a retaining part for retaining the device in place over the region of the patient's skin during an activation cycle. A light source is arranged to illuminate the patient's skin from the rear of the device. A (Continued)

control system is configured to vary the output of the light source with respect to time in accordance with a preconfigured output sequence.

15 Claims, 8 Drawing Sheets

(51) Int. Cl.
*A61M 37/00* (2006.01)
*A61K 39/00* (2006.01)
*A61B 17/00* (2006.01)

(52) U.S. Cl.
CPC .... *A61K 39/00* (2013.01); *A61K 2039/55555* (2013.01); *A61M 2037/0023* (2013.01); *A61N 2005/0626* (2013.01); *A61N 2005/0627* (2013.01); *A61N 2005/0629* (2013.01); *A61N 2005/0645* (2013.01)

(58) Field of Classification Search
CPC ............ A61N 5/062; A61N 2005/0652; A61N 2005/063; A61N 5/0613; A61N 5/0616; A61N 5/06; A61M 2037/0023; A61M 37/0015
See application file for complete search history.

(56) References Cited

U.S. PATENT DOCUMENTS

| | | | |
|---|---|---|---|
| 6,334,856 B1 | 1/2002 | Allen et al. | |
| 6,443,978 B1 | 9/2002 | Zharov | |
| 8,454,991 B2 | 6/2013 | Woo et al. | |
| 2006/0036209 A1 | 2/2006 | Subramony et al. | |
| 2006/0167532 A1 | 7/2006 | Parker | |
| 2006/0173514 A1* | 8/2006 | Biel | A61F 13/023 607/88 |
| 2006/0271131 A1 | 11/2006 | Passy et al. | |
| 2007/0088248 A1* | 4/2007 | Glenn | A61B 17/20 604/46 |
| 2007/0288071 A1 | 12/2007 | Rogers | |
| 2009/0041810 A1* | 2/2009 | Andrianov | A61K 9/0021 424/400 |
| 2009/0143842 A1 | 6/2009 | Cumbie et al. | |
| 2010/0256064 A1 | 10/2010 | Woolfson et al. | |
| 2011/0052694 A1 | 3/2011 | Stinchcomb et al. | |
| 2011/0152748 A1 | 6/2011 | Della Rocca et al. | |
| 2011/0160069 A1 | 6/2011 | Corrie et al. | |
| 2011/0288508 A1 | 11/2011 | McCarron et al. | |
| 2013/0103123 A1* | 4/2013 | Khan | A61N 5/0624 607/90 |
| 2014/0330196 A1* | 11/2014 | Ingman | A61N 1/0476 604/21 |

FOREIGN PATENT DOCUMENTS

| | | |
|---|---|---|
| WO | 96/07432 | 3/1996 |
| WO | 99/64580 | 12/1999 |
| WO | 00/54802 | 9/2000 |
| WO | 01/51087 | 7/2001 |
| WO | 2005/072630 | 8/2005 |
| WO | 2006/016364 | 2/2006 |
| WO | 2007/030415 | 3/2007 |
| WO | 2009/008988 | 1/2009 |
| WO | 2010/070628 | 6/2010 |
| WO | 2010/078929 | 7/2010 |
| WO | 2012/074454 | 6/2012 |
| WO | 2012/154284 | 11/2012 |

OTHER PUBLICATIONS

International Search Report dated Oct. 13, 2014, in Application No. PCT/EP2014/068236.
Search Report under Section 17(5) dated Feb. 19, 2014 in Application No. GB1315288.9.
Communication Pursuant to Article 94(3) EPC dated Mar. 23, 2018 in European Application No. 14 755 836.5.

* cited by examiner

ANTIGEN DELIVERY DEVICE AND METHOD

TECHNICAL FIELD

The present invention relates to an antigen delivery device for activating light-induced rupture of endocytic vesicles in target cells of a patient so as to effect delivery of an administered antigen, and also to a method of activating said light-induced rupture using the device.

INTRODUCTION

It is known to deliver an antigen to a patient by administering the antigen to a region of the patient's skin together with a photosensitising agent, allowing time for the antigen and photosensitising agent to migrate to target cells in the dermis or other tissue, where endocytic vesicles containing the antigen form in the target cells, and then to shine a light on the patient's skin to trigger the rupture of these endocytic vesicles, and thereby deliver the antigen to the cytosol of the target cells.

Typically there is a delay of anything up to 36 hours or more between the administering of the antigen and the photosensitising agent (systemically), and the light-induced rupturing of the endocytic vesicles, in order to allow time for the components to make their way to the target cells and to be taken into the cells by endocytosis to form the endocytic vesicles. Currently, a free-standing light source, for example, provided in the medical centre where the antigen is administered, which would usually be operated by specialist medical staff, is used to provide the light for activating the rupture of the endocytic vesicles. The patient receiving the antigen must either wait around or return to the medical centre to be treated with the light.

There is the potential for the patient to miss this last part of the activation cycle, or to receive the light too early or too late after a prescribed time, i.e. when the activity of the photosensitising agent may not be optimum, either as a result of human errors or through delays in treating the patient. Such variations in the procedure could have implications on the delivery of the antigen and the reliability of the response it creates.

It would be desirable to provide a device that can simplify the delivery of the antigen to patients and potentially reduce the dependency on such medical centres.

SUMMARY OF THE INVENTION

Thus according to a first aspect there is provided a device for activating light-induced rupture of endocytic vesicles in target cells of a patient so as to effect delivery of an administered antigen to cytosol in the target cells. The device is adapted to be worn by a patient over a region of the patient's skin where an antigen and a photosensitising agent has been or is to be administered. The device comprises a rear surface that is configured to be worn against the patient's skin, a retaining part for retaining the device in place over the region of the patient's skin during an activation cycle, a light source arranged to illuminate the region of the patient's skin from the rear surface of the device, a control system to control the operation of the light source after initiation of the activation cycle, and a power supply to power the light source and the control system. The control system is configured to vary the output of the light source with respect to time in accordance with a pre-configured output sequence. The output sequence includes an initial stage where the output of the light source is set to be zero or generally below that which could deliver a light dose that can activate light-induced rupture of endocytic vesicles. This is to allow time for the antigen and photosensitising agent to reach the target cells. The output sequence also includes a later stage where the output of the light source is set to deliver a light dose which can activate light-induced rupture of the endocytic vesicles. This is for effecting the delivery of the administered antigen to the cytosol of the target cells.

The device offers many benefits. As it is worn by the patient for an extended period, which is from the start of an activation cycle when an antigen, which might be a vaccine, is administered (or shortly thereafter) until after the light-induced rupture of the endocytic vesicles has been effected, the delivery of the administered antigen can be more carefully controlled, in particular without requiring input from specialists at medical centres.

The control system is configured to vary the output of the light source with respect to time in accordance with a pre-configured output sequence, i.e. the output of the light source is fully automated once the activation cycle has been initiated. The output sequence may be set according to the particular antigen that is to be delivered and/or the photosensitising agent used to effect the light-induced rupture. Once the activation cycle is initiated, the patient has to take no further action to ensure the proper delivery of the antigen. Thus this can avoid the potential problems which might result from human error or delays in treating the patient.

The device offers significant potential as a delivery solution for delivering an antigen reliably to a large number of patients that may not have access to medical centres, for example, in remote areas or third world countries, or where it may be desirable to avoid the involvement of medical centres.

The device is preferably arranged to be disposable, for example, it may be used once and thrown away by the patient. It could also be arranged to be returned to the manufacturer or distributor (e.g., the medical centre or government department) for re-charging and re-use by another patient.

The device may be in the form of an electronic patch, a watch or bracelet, or some other device that can be worn on an appropriate part of the body, for example, a wrist, an arm, a shoulder, a leg, an ankle, etc., where it is comfortable to wear continuously for an extended period, e.g. for more than three hours and possibly up to 96 hours or so, more preferably 6 to 48 hours.

The retaining part might be a strap, for example, incorporating an adjustment buckle, a fastener, an adjustment mechanism, hook and eye material or some other re-connectable system, e.g. similar to known watch straps, for adjusting the length of the strap(s) to fit the device securely on the patient. The retaining part may comprise a broader web of material that is worn around a limb of the patient, for example, as a sleeve or cuff, or conceivably it could also be in the form of a glove or sock. The retaining part may also comprise an adhesive for adhering the device, at least temporarily, to the patient's skin. This may be in addition to other measures to retain the device in place for the duration of the activation cycle.

According to another aspect there is also provided a method of activating light-induced rupture of endocytic vesicles in target cells of a patient so as to effect delivery of an administered antigen to cytosol in the target cells. The method comprises administering an antigen and a photosensitising agent to a region of the patient's skin, wearing a device (for example, a device as described above) for activating the light-induced rupture of endocytic vesicles in the target cells, initiating an activation cycle on the device for the light-induced rupture of the endocytic vesicles, and during the activation cycle, illuminating the region of the patient's skin from the rear surface of the device in accordance with a pre-configured output sequence controlled by a control system of the device. The output sequence includes an initial stage where the output of the light source is set to be zero or generally below that which could deliver a light dose that can activate light-induced rupture of endocytic vesicles. This is to allow time for the antigen and photosensitising agent to reach the target cells. The output sequence also includes a later stage where the output of the light source is set to deliver a light dose which can activate light-induced rupture of the endocytic vesicles. This is for effecting the delivery of the administered antigen to the cytosol of the target cells.

The present invention also extends to the use of the above-described device to deliver an administered antigen, or to administer and deliver an antigen, through wearing and activating the device.

The antigen may be administered to the region of the patient's skin before the device is worn by the patient. For example, a swab containing the antigen may be wiped across the region of the patient's skin, or a cream containing the antigen may be rubbed into the region of the patient's skin, prior to the wearing of the device.

The photosensitising agent may be administered simultaneously with the antigen through the administering of a pharmaceutical preparation that contains both the antigen and the photosensitising agent. In some instances it may be more desirable to administer the antigen and photosensitising agent separately.

Additional components, such as one or more adjuvants for example, may be administered with one or other of the antigen or the photosensitising agent, or both. Also more than one antigen may be administered to the region of skin, possibly at different times. Similarly, more than one photosensitising agent may be administered, possibly at different times or simultaneously.

The antigen and/or photosensitising agent may be present in a form that delays its release into the body, for example, it may be combined with a substance or encapsulated within a dissolvable coating.

Preferably, the device includes a drug administering portion for administering the antigen and/or photosensitising agent. The drug administering portion may be provided on the rear of the device, close to or in contact with the region of the patient's skin when the device is worn.

In one example, the drug administering portion comprises a patch that can release, in a controlled manner, the antigen and the photosensitising agent, either sequentially or simultaneously. This patch may be in the form of a gel or cream provided within a pocket of the rear of the device. More preferably the patch comprises micro-needles and may be mounted on a mechanism for deploying the micro-needles.

These micro-needles may be coated in a pharmaceutical preparation containing the antigen and photosensitising agent (and possibly other components such as an adjuvant or stabiliser) or the micro-needles may be made of the pharmaceutical preparation itself, preferably in combination with a dissolvable polymer that can provide the solid structure of the micro-needles. In this way, the pharmaceutical preparation can become deposited within the skin through physical delivery of the coating or through dissolution of the micro-needles. In another example, micro-needles may be connected to a reservoir of a pharmaceutical preparation containing the antigen and photosensitising agent, either mixed or stored separately, that is then delivered to the patient through conduits within the micro-needles.

The control system may be configured so that the act of administering at least the antigen and/or the photosensitising agent initiates the activation cycle. This may be achieved automatically, for example, by pressing a button on the device to administer the antigen and/or the photosensitising agent that also initiates the activation cycle in the control system. The act of pressing the button may also deploy a micro-needle or patch of micro-needles into the region of skin of the patient. In another example, a protective strip may cover the antigen and/or photosensitising agent to seal it from ambient conditions, and the act of removing the protective strip may initiate the activation cycle, e.g. through activating a contact in an activation circuit. The removal of the protective strip may also reveal areas of adhesive to help secure the device to the patient.

In a further example, the patient may have to follow a set of instructions that appear on a screen of the device, and the act of pressing a button in response to an instruction may initiate the activation cycle. Initiating the activation cycle by pressing a button is preferably used where the antigen and/or the photosensitising agent has been administered prior to the wearing of the device.

The light source may comprise an electronic light emitting device, such as an LED, lamp or laser device, for example, a laser diode. The light source may comprise one or more of such electronic light emitting devices, which might all be the same or have different emission properties. Light may be delivered to the patient's skin directly from the light source, or it might be conveyed by a light guide. In one example where the device is provided with a drug administering portion in the form of micro-needles, the micro-needles themselves may act as light guides to convey the light to the target cells.

An appropriate light source is selected according to the photosensitising agent and target cells, i.e. one with an emission spectrum corresponding to the absorption properties of the photosensitising agent and an output high enough to achieve the required light dose to rupture the endosome membranes. It may emit light in the visible spectrum, or emit light to the side of the visible range, according to the requirements of the photosensitising agent. Most preferably the emission is within the visible spectrum since this avoids additional health and safety considerations. In one example, it may emit light in the blue region of the spectrum. In another, for example, where deeper cells are being targeted, it may use a red light to activate the light-induced rupture within the target cells.

The light output may comprise a single emission peak or several emission peaks. In a further example, the device may incorporate more than one type of light source for activating light-induced endocytic vesicle rupture in different types of target cell, for example, cells at different depths within the skin tissue structure. In another, the light source with the plurality of emission peaks may activate a first oxidation reaction in a first photosensitising agent and a second oxidation reaction in a second photosensitising agent.

The rear surface of the device is configured to be worn against the patient's skin. For example, the rear surface may be shaped to follow the normal curve of the skin in the particular region. It may be provided by a housing that encloses the drug administering portion and/or the light source, so that these parts are not visible when the device is worn. It might be desirable to provide a visual feedback or cue to the patient when the light source is activated, e.g. through a glow being visible from under the device.

The device also contains a power supply. The power supply may be in the form of a battery or battery pack provided within a housing of the device. It is also envisaged that the power supply may be provided in a second housing that is connected to a first housing via an electrical lead, for example, where it is preferred to wear the power supply, which may be comparatively heavy, separately from the part of the device containing the light source.

In one example, the act of removing an insulating strip from between the contacts of a battery and an electrical pick-up contact, or in some other way, connecting up the power supply, initiates the activation cycle in the control system.

The control system may comprise a hard-wired logic circuit or, more preferably, it may comprise a programmable controller that is preconfigured with a set of instructions to vary and control the output of the light source with respect to time in accordance with an output sequence. Those instructions may be non-adjustable so that the output sequence followed is entirely pre-set into the device. In other examples, the output sequence may be governed by a combination of pre-stored instructions and input signals, e.g., from feedback that is obtained during the activation cycle. The input signals may indicate the migration of the photosensitising agent or other component (e.g. through monitoring fluorescence), the oxidation of the photosensitising agent (e.g. again through monitoring changes in fluorescence) or it may indicate the light-absorption of the patient's skin, in order to take these factors into account to fine tune the output of the light source and thereby ensure optimal delivery of the antigen for a given patient. Thus the control system may comprise algorithms that are based on such input signals which adjust the output sequence automatically, for example, by extending a minimum period of delay according to the monitored fluorescence, e.g. where the migration is slower than a threshold, or extending the period of illumination or increasing the intensity of the light source, e.g., where the fluorescence of the photosensitising agent has not dropped off as expected or where the patient's skin absorption exceeds a threshold level.

The algorithms may comprise criteria such as minimum output light intensity of the light source and duration of illumination, that may all serve to define the required light dose for a given skin depth. The light dose required may vary according to the intensity of the light source's output selected. For example, it might be lower for light doses that are delivered over a longer period compared to a shorter period, though the reduced intensity required to deliver the light dose over a longer period may be more comfortable for the patient. The intensity may be selected for a given photosensitising agent, for example, one may have better absorption properties for the light source or be easier to activate than another photosensitising agent.

The control system is pre-configured so that the output sequence includes an initial stage after the activation cycle has been initiated where the output of the light source is set to be zero (i.e. the light source is off or the light is completely shielded) or generally below an intensity that can activate light-induced rupture of the endocytic vesicles of the target cells. This is to provide time for the antigen and/or photosensitising agent to reach the target cells. The antigen must, of course, also have been taken in by the target cells through endocytosis to form the endocytic vesicles containing the antigen.

The activation of the photosensitising agent is a combination of both the intensity of the light emitted and the time that the light is radiated for. Thus, by "generally below" it is meant that the intensity should stay either below that which can activate the light-induced rupture or, if it should pulse above this level, only to do so for a time that is of negligible detrimental effect to the photosensitising agent.

While exposing the photosensitising agent to light prematurely can cause deterioration in its effectiveness, in some instances it may be beneficial to provide one or more pulses of light, ideally at a level below that which can activate the light-induced rupture, during this initial stage. Where, for example, an adjuvant is also administered, such a pre-activation pulse of light might improve the patient's response to the antigen.

As the device is worn for the entire period of the activation cycle, the device itself will also help to shield the region of skin where the antigen and photosensitising agent have been administered. This not only keeps the natural light out from this region during the activation cycle, but can also help to protect that region against the ingress of dirt, etc., which might cause an infection risk.

The control system is also pre-configured so that the output sequence includes a later stage where the output of the light source is set to be at an intensity above that which can activate light-induced rupture of the endocytic vesicles. This is the stage of the output sequence that effects the delivery of the administered antigen inside the target cells by causing the antigen-containing endocytic vesicles to rupture and thereby deliver the antigen into the cell's interior. The period of time at such an intensity for the light source will be dependent on many factors, such as the intensity of light used, the type of photosensitising agent, the target cells etc.

The device may be provided with an alarm, such as an audible alarm or a visual signal, such as a coloured light or screen display, to indicate that the activation cycle has been completed and the patient is free to remove the device.

The control system is preferably also configured so that it turns off the light source once the activation cycle has been completed.

BRIEF DESCRIPTION OF THE DRAWINGS

Certain preferred embodiments will now be described in greater detail by way of example only and with reference to the accompanying drawings in which.

DETAILED DESCRIPTION

The prior art technology for light-directed drug delivery was developed by PCI Biotech AS to introduce therapeutic molecules in a biologically active form specifically into diseased cells. Molecules are taken into the cell by endocytosis, and this can include most types of macromolecules (such as proteins and nucleic acids), drugs carried by antibodies or nanoparticles, as well as some small molecule drugs.

The basis of the technology is a light-induced rupture of endocytic vesicles, releasing endocytosed molecules into the cell cytosol, from where they can reach their intracellular target of action, realizing their therapeutic potential. The process uses photosensitising agents that specifically localise in the membranes of endocytic vesicles, opening these membranes by an oxidative process after illumination.

Figure 1A:
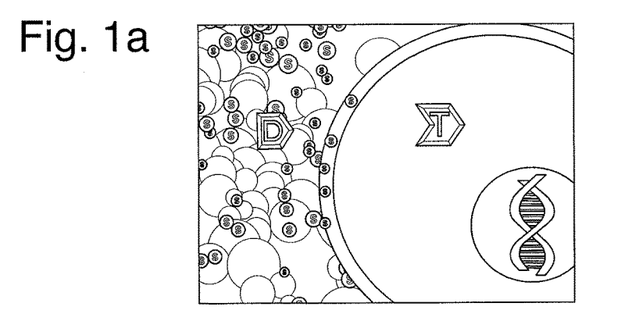
FIGS. 1a to 1d illustrate schematically the process behind light-directed drug delivery.
Figure 1B:
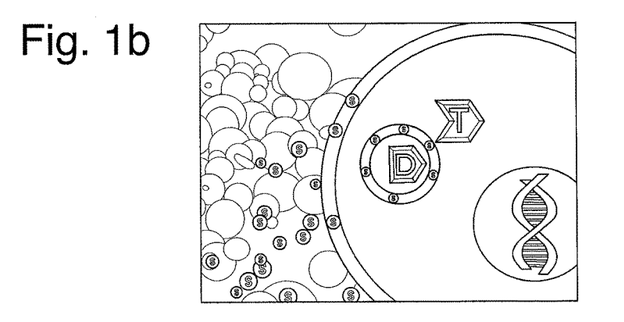
Figure 1C:
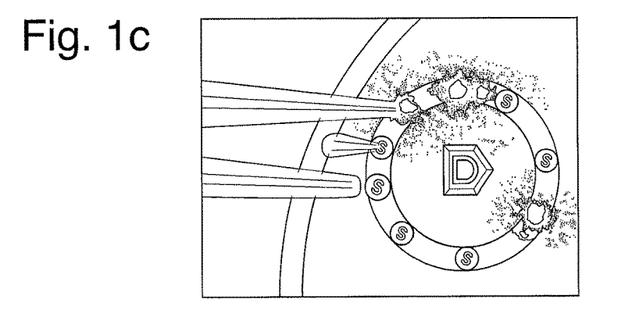
Figure 1D:
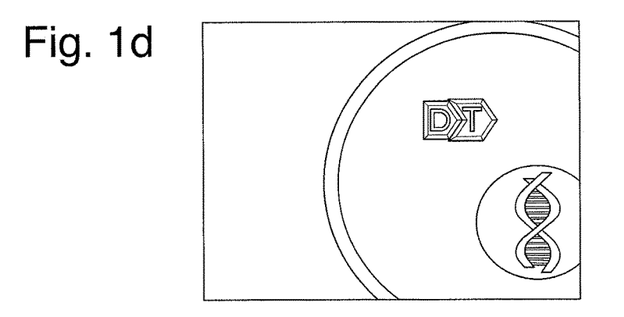

The process behind the drug delivery is illustrated with reference to FIGS. 1a to 1d, which illustrates a known systemic drug delivery process. In FIG. 1a, the photosensitising agent (S) and the drug (D) are shown as they are injected into the body and carried by the blood stream to the target cell containing the therapeutic target molecule (T). In FIG. 1b, the photosensitising agent and the drug are shown as they are taken up by the cell, but the drug is unable to reach the target, as it is encapsulated in an endosome (with the photosensitising agent in the membrane). In FIG. 1c, the target cells are illuminated and this Illumination activates the photosensitising agent in the membrane of the endosome. The membrane is destroyed and the drug is released. As shown in FIG. 1d, the drug molecule is then able to bind to its therapeutic target, initiating a therapeutic response.

In such systemic drug delivery processes, the photosensitising agent is activated by a free-standing light source after the antigen and photosensitising agent have been administered and given sufficient time to reach the target cells. This is typically somewhere in the region of 96 hours after administering the drugs depending on the antigen and/or photosensitising agent combination and the target cells involved.

Figure 2:
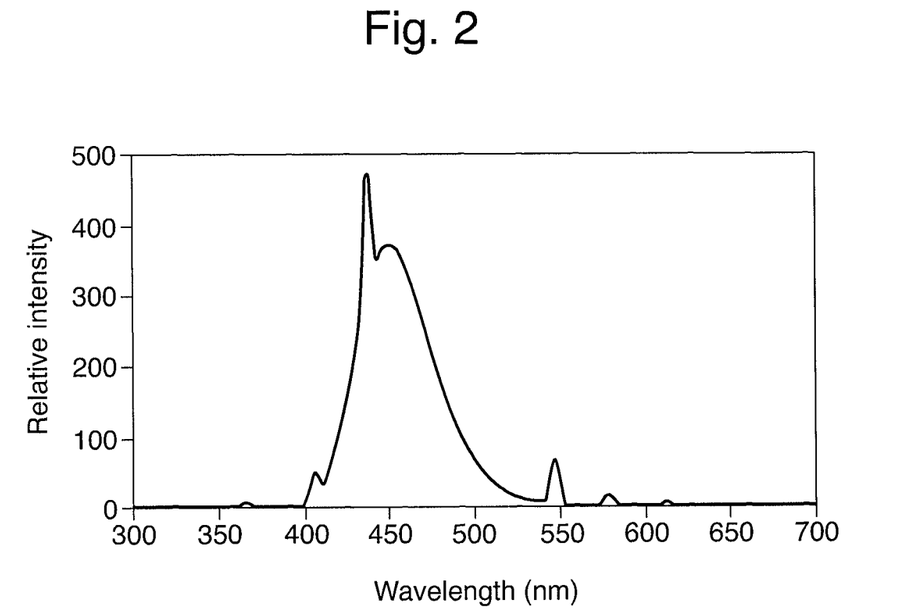
FIG. 2 illustrates an example of a light emission spectrum from a prior art light source.

An example of a current prior art light source is one distributed under the name LumiSource®, which is a free-standing light source that is available through PCI Biotech AS. It is designed specifically to provide homogeneous illumination of living cells in an invitro setting. The lamp comprises light tubes with reflectors designed to provide stable, homogeneous fluency rates over a defined illumination area of 45×17 cm. In addition to the tubes, the lamp also comprises a removable top plate and a shutter. The LumiSource® is provided with 4 light tubes (4×18 W Osram L 18/67, Blue) emitting mainly blue light with a peak wavelength of approximately 435 nm. These light tubes are intended for use in the PCI technology described above together with the photosensitising agent $TPPS_{2a}$ (meso-tetraphenyl porphyrin disulphonate) LumiTrans® (also supplied by PCI Biotech AS). Another photosensitising agent might be $TPCS_{2a}$ (meso-tetraphenyl chlorin disulphonate-Amphinex) which also is activated by blue light. The light emission from LumiSource® is selected for optimal excitation of LumiTrans® (see. FIG. 2 which illustrates an example emission spectrum for standard light tubes 4×18 W Osram L 18/67, blue). By way of example, the irradiance of the illumination area in the middle of the field in this prior art light source is around 13.5 $mW/cm^2$ (measured by IL 1700 Research Radiometer from International Light).

In accordance with the present disclosure, there is provided a device that can be worn by a patient to perform the light-induced rupture of endocytic vesicles in target cells of the patient. In this way, light-directed delivery of an administered antigen to the patient (e.g., a vaccine, which can promote a health giving response in the patient) can be achieved without the intervention of a medical specialist.

Figure 3A:
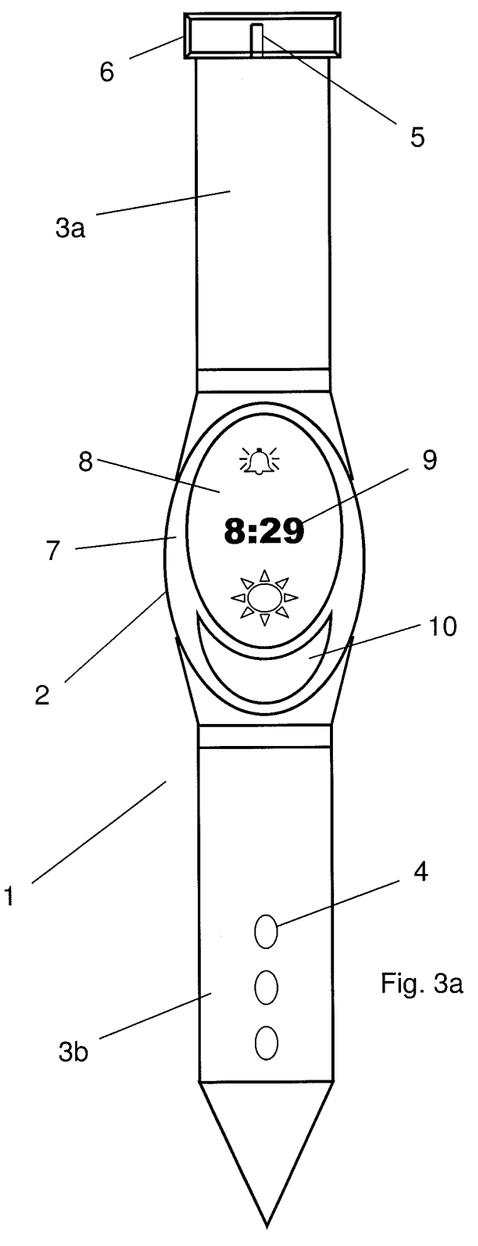
FIGS. 3a and 3b illustrate a first embodiment of the device from the front and from the side respectively.
Figure 3B:
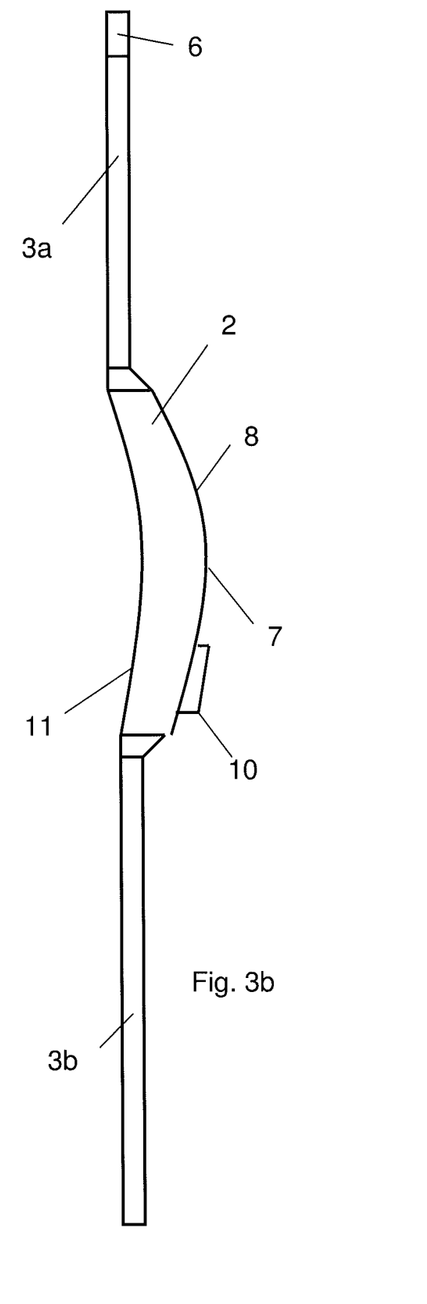

In one example, illustrated in FIG. 3a, the device 1 is substantially in the form of a watch. FIG. 3b shows a side elevation of the device 1 in FIG. 3a. It is intended to be worn by a patient for an extended period of time against a region of the patient's skin where an antigen and a photosensitising agent have been or are to be administered.

Figure 4:
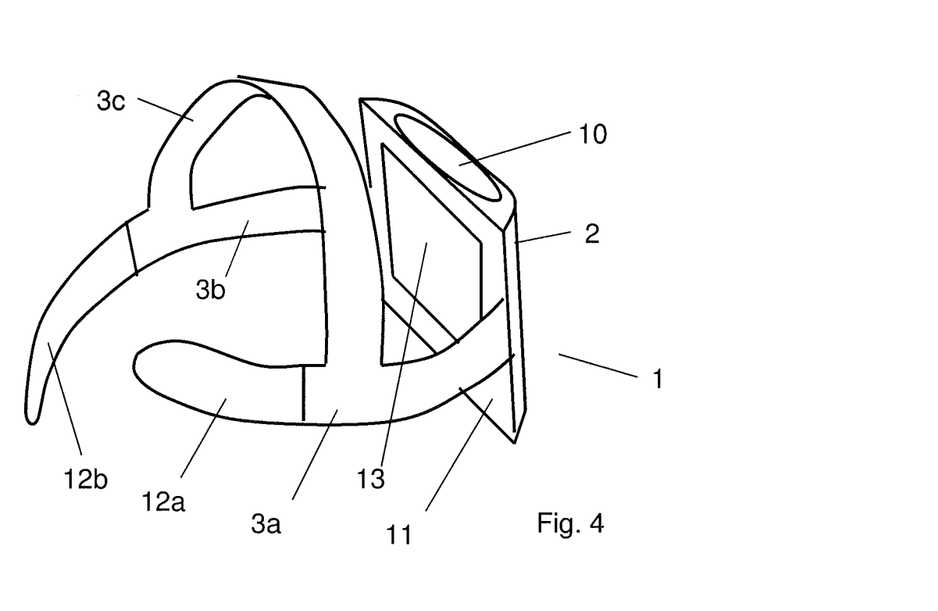
FIG. 4 illustrates a perspective view of a further embodiment.

In the embodiment, the device 1 comprises a housing 2 having an appearance that is not too dissimilar from a conventional watch case. It is provided with a retaining part, for example, straps 3a and 3b to hold the device 1 in place. The device 1 may be secured, for example, on the wrist of the patient, but equally it could be secured on the arm, ankle or leg of the patient as preferred. One preferred region of a patient is at the top of their arm where it meets the base of the shoulder complex. For such regions a different strap arrangement may be required to secure the device 1 comfortably on the patient (for example, as shown in FIG. 4).

In FIG. 3a, the straps 3a, 3b, are shown similar to traditional watch straps, but these could take many forms. In the example, holes 4 are provided in one strap 3b for receiving a pin 5 of an adjustable buckle 6 provided at one end of the other strap 3a, so as to provide a range of fitting/tightness positions. Other forms of strapping could, of course, be used, for example, laces that are tied around the patient, different forms of closure mechanism that connect or are adjustable to change the size of the retaining part, the use of hook and eye materials on opposite straps or part to form a fully adjustable connection (FIG. 4), etc. are just some of the possibilities The strapping should be sufficiently flexible in length to fit all sizes of patient that are likely to be encountered. It is also envisaged that the housing 2 of the device 1 may be integrated into a sleeve or cuff, for example, that is preferably elasticated for wearing on a limb of the patient (FIG. 5), possibly with the assistance of an adjustable strap to tighten it when in place on the patient. An adhesive patch may also be provided to stick the device 1 temporarily to the patient.

On the front surface 7 of the device 1, i.e., the surface that the patient sees, there may be a display 8 that shows either the time remaining 9 or the time of the activation cycle that has elapsed, as visual feedback to the patient. The front surface 7 of the device may also be provided with a button 10 for initiating the activation cycle and/or otherwise controlling the device 1. The form and position of the display 8 and/or button 10 is, of course, not limited to that shown and may comprise other forms and arrangements; for example, rather than a numeric display, the display 8 may provide a graphic illustration of the stage of the activation cycle, or the button 10 (or buttons), when present, may be provided on a side surface of the device 1 rather than the front surface 7.

The device 1 could also comprise a touch sensitive screen in place of buttons. It could also comprise a protective cover plate or be activated by a remote fob if it was preferred that the patient should not have access to such buttons after the activation cycle has been initiated.

The rear surface 11 of the device 1 is configured to be worn against the patient's skin. Depending on the size of the device 1, the rear surface 11 may be flat like a conventional watch back or it may be concave in one or two dimensions, in order to follow the contours of the patient's body (in FIG. 3b, the device 1 is curved in a longitudinal direction but it may have curvature in a width direction too). It should be comfortable to wear continuously for an extended period, for example, for between 3 to 100 hours, more preferably 6 to 48 hours, though in some circumstances the device 1 may need to be worn for longer.

FIG. 4 shows another preferred embodiment that is intended to be worn at the top of a patient's arm. In this embodiment, the straps 3a, 3b are intended to be fitted around the top of the arm, where the deltoid muscle reaches the bicep, and these straps 3a, 3b are connected by a further strap 3c that fits over the shoulder. The arm straps 3a, 3b are provided with patches of opposite types of hook/eye material 12a, 12b that can overlap one another to hold the device 1 securely against the patient's arm. Other arrangements of straps and harnessing would also be possible.

On the rear surface 11 of the device 1 there is provided a light emitting region 13 that is worn against the patient's skin. The light emitting region 13 may also comprise a drug administering portion, as will be explained in more detail below.

Figure 5:
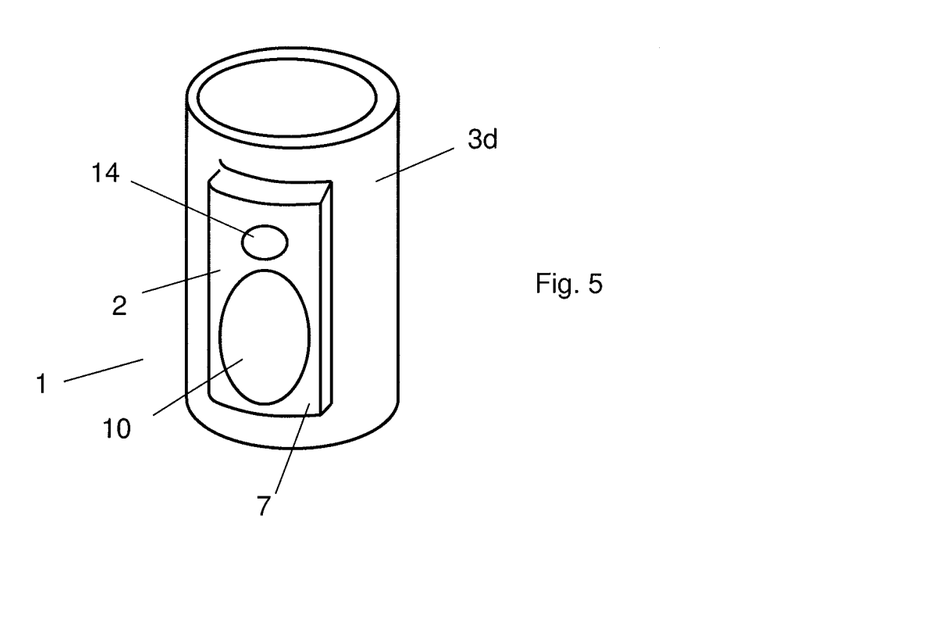
FIG. 5 illustrates a perspective view of another embodiment using a sleeve to hold the device in place.

FIG. 5 shows a further preferred embodiment where the device 1 is incorporated into an elasticated sleeve 3d that can be pulled up over a limb. The sleeve 3d may also take the form of a wide strip of material that is wrapped around the limb and held in place with cooperating pieces of hook and eye material, in much the same way as a blood pressure monitoring cuff would be fitted around an arm of a patient. In further arrangements, one or more straps may also be provided around the sleeve to pull the sleeve tight.

In the embodiment of FIG. 5, the housing 2 is provided with a button 10 to initiate the activation cycle. It is also provided with a light 14 to indicate either when the activation cycle has finished (it might comprise a green LED for example to indicate to the patient that the device 1 is safe to remove) or to indicate which stage the device 1 is at (it might shine a first colour to indicate that it is ready for use or has initiated the activation cycle, and emit light of a second colour when the activation cycle is complete). The button 10 itself or other part of the device 1 may be illuminated in place of providing the light 14.

Any of the devices 1 described may also include an audible alarm, and/or a vibratory device to provide a physical alarm, to indicate when the activation cycle is complete.

Figure 6A:
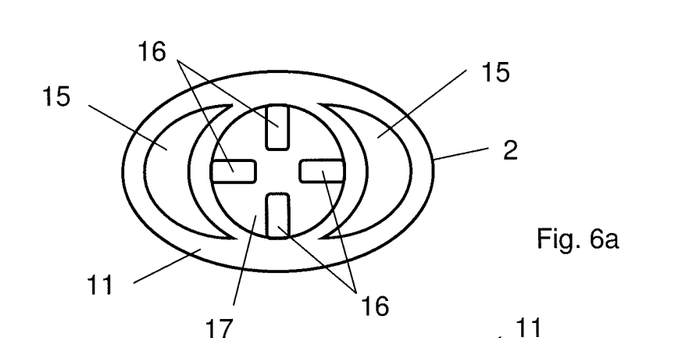
FIGS. 6a to 6c illustrate examples of rear surfaces of three further devices.
Figure 6B:
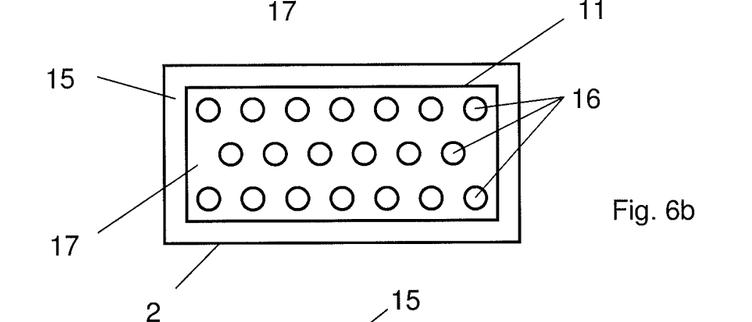
Figure 6C:
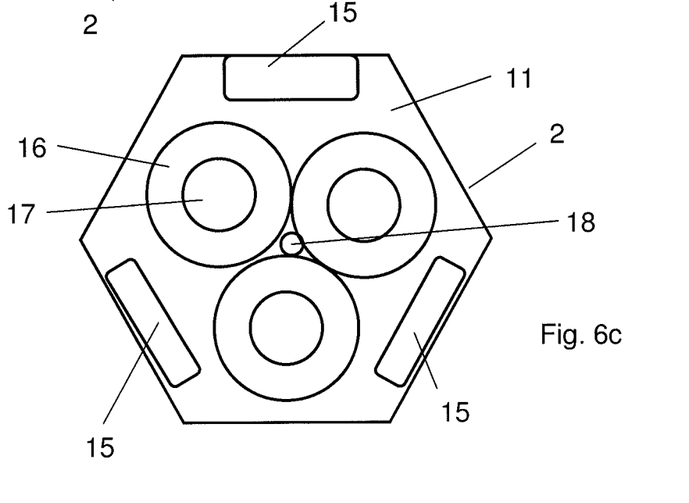

The device 1 comprises a light source, which is provided within the housing 2 and arranged to illuminate the region of the patient's skin from the rear surface of the device. FIGS. 6a to 6c show some example arrangements of the rear surface 11 of the device 1.

In FIG. 6a, the device 1 comprises an oval housing 2. On the rear surface 11 are provided two adhesive patches 15 for adhering the device 1 to the skin of the patient for the duration of the activation cycle. These are arranged on either side of a region that has four light emitting devices 16, for example, LEDs or laser diodes, as the light source which is provided within an area that also comprises a drug administering portion 17. In one example where the drug administering portion comprises transparent micro-needles, the light emitting devices may be mounted within the device 1 behind the micro-needles and emit their light through the micro-needles themselves. Alternatively light guides within the drug administering portion may direct light to the patient's skin.

In order to avoid discomfort from heat, it may be preferable to locate the light source(s) towards or on the front of the device and use light guides to carry the light to the rear of the device and preferably diffuse the light. In this way a heat dissipating part or heat sink may be incorporated into the design of the device, for example, the front of the device (which avoids contact with the skin).

In FIG. 6b, an example of a rear surface 11 is shown for a device 1 comprising a rectangular housing 2. In this example, an adhesive patch 15 surrounds an array of light emitting devices 16 provided within a drug administering portion 17.

In FIG. 6c, a further example of a rear surface 11 is shown for a device 1 comprising a hexagonal housing 2. In this example, three adhesive patches 15 are provided on the rear surface 11 to help retain the device 1 on the patient. In this embodiment the three drug administering portions 17 each surround a light emitting device 16. The light emitting device 16 includes a ring-shaped light diffuser.

Further illustrated in FIG. 6c is a sensor 18 provided in the rear surface 11. This might be for monitoring properties such as the fluorescence of a component or the absorption of the skin as will be explained in more detail below. One or more such sensors 18 could be provided on any of these examples.

As indicated by FIGS. 6a to 6c, the housing 2, any adhesive patch 15 (if present), light emitting device 16 or drug administering portion 17 (if present), may comprise many different forms and arrangements, and are not limited to the forms and arrangements in the examples shown. The light source may comprise a plurality of light emitting devices and/or may direct the light through a diffuser or light guide in order to provide a more uniform level of illumination.

The light source may be capable of emitting at an intensity that produces an irradiance equivalent to that achievable to the free standing light sources, for example, the light intensity may be an irradiance in the region of 0.005-500 mW/cm$^2$, e.g. 0.01-100 mW/cm$^2$, 0.05-50 mW/cm$^2$, 0.1-25 mW/cm$^2$ or 0.5-20 mW/cm$^2$. In another example the irradiance is in the range of 0.05-20 mW/cm$^2$. Preferably the light intensity produces an irradiance of around 10 mW/cm$^2$. In some tests, lower levels of irradiance of around 1 to 3 mW/cm$^2$ showed promise where longer exposure times are used, such levels being more easily achieved by single LED sources.

The light dose may be at least 0.05 J/cm$^2$, and may have a maximum of 100 J/cm$^2$, e.g. 0.1-50 J/cm$^2$, 0.5-10 J/cm$^2$, 1-7 J/cm$^2$, or 2.8 and 4.8 J/cm$^2$. Preferably the light dose is 3.5 J/cm$^2$. In one set of experiments, light doses of between 0.24 and 7.2 J/cm$^2$ were investigated for a fibre coupled LED light source having a peak emission of 430-435 nm and producing irradiance levels of 0.05-20 mW/cm$^2$, for example, 2.0 mW/cm$^2$. Peak levels of immune response with TPPS$_{2a}$ were seen for light doses of between 0.48 and 3.6 J/cm$^2$.

In one example the light source produces light with an intensity of at least 5 mW/cm$^2$, more preferably at least 10 mW/cm$^2$. This might be where a light dose is given for a period of between 2 and 20 minutes, more preferably between 5 and 10 minutes. However the illumination time could also be extended in order to bring down the intensity. For example, if the illumination times were extended to up to 12 hours, then it may be possible to reduce the intensity to less than 1 mW/cm$^2$, more preferably between 0.05 and 0.5 mW/cm$^2$ or less. Such times might be suitable for a photosensitising agent such as TPPS$_{2a}$ using a light source with an emission spectrum having a peak at about 435 nm.

The required intensity of the light source will be dependent on, amongst other things, the particular photosensitising agent (e.g. how much light it requires, either as a threshold level, total amount of light energy or other activation characteristic) and how it responds to the emission spectrum of the particular light source (e.g. the alignment of the emission and absorption characteristics). It will also be dependent on the duration of the illumination (e.g. whether the light dose is delivered over a short or long period) and characteristics of the patient (e.g. dark or light skin, depth of the target cells, etc.).

The light source may have a main emission peak in the visible spectrum, e.g. have outputs in the red, yellow, green, blue regions, more preferably in a blue or red region of the spectrum. In one preferred example, it has an emission spectrum substantially similar to that illustrated for the LumiSource® lamp illustrated in FIG. 2 with an emission peak in the 400 to 500 nm range, more preferably centred between 420 and 470 nm with a main peak at about 430 nm (±10 nm) and preferably a secondary peak at 450 nm (±10 nm). In other examples, the device 1 may include two or more types of light emitting device, each type having a different emission spectrum. Other photosensitising agents may be activated by yellow, green or red light, for example. For red light, a suitable source of illumination might be a laser diode with a peak emission of around 652 nm ±10 nm.

Tests have been performed using an LED source having an emission peaks in the range of 435 nm to 430 nm. One advantage noticed with such LED light sources is that the LEDs can produce more energy in the spectral range where the photosensitising agent has a large coefficient of absorption than has been observed for the previously used lamps. This means that less power is required from the power source to achieve a prescribed irradiance or fluence level, bringing the levels required within the reach of conventional battery arrangements.

The adhesive patch(es) in FIGS. 6a to 6c may be in place of or in addition to the retaining parts illustrated in FIGS. 3a to 5 (i.e. the adhesive patch(es) could be the sole retaining part). Thus the devices 1 of FIGS. 6a to 6c may also comprise one or more straps, webs, sleeves or other retaining part to hold the device 1 in place on the patient.

The drug administering portion 17 may take many forms. In one example it comprises a patch in the form of a gel or impregnated foam pad that allows the drug to transfer into the skin of the patient through contact. More preferably the drug administering portion 17 comprises a micro-needle, more preferably a patch of micro-needles, in order to aid the administration of the drug (e.g., the antigen, photosensitising agent and possibly an adjuvant).

Figure 7:
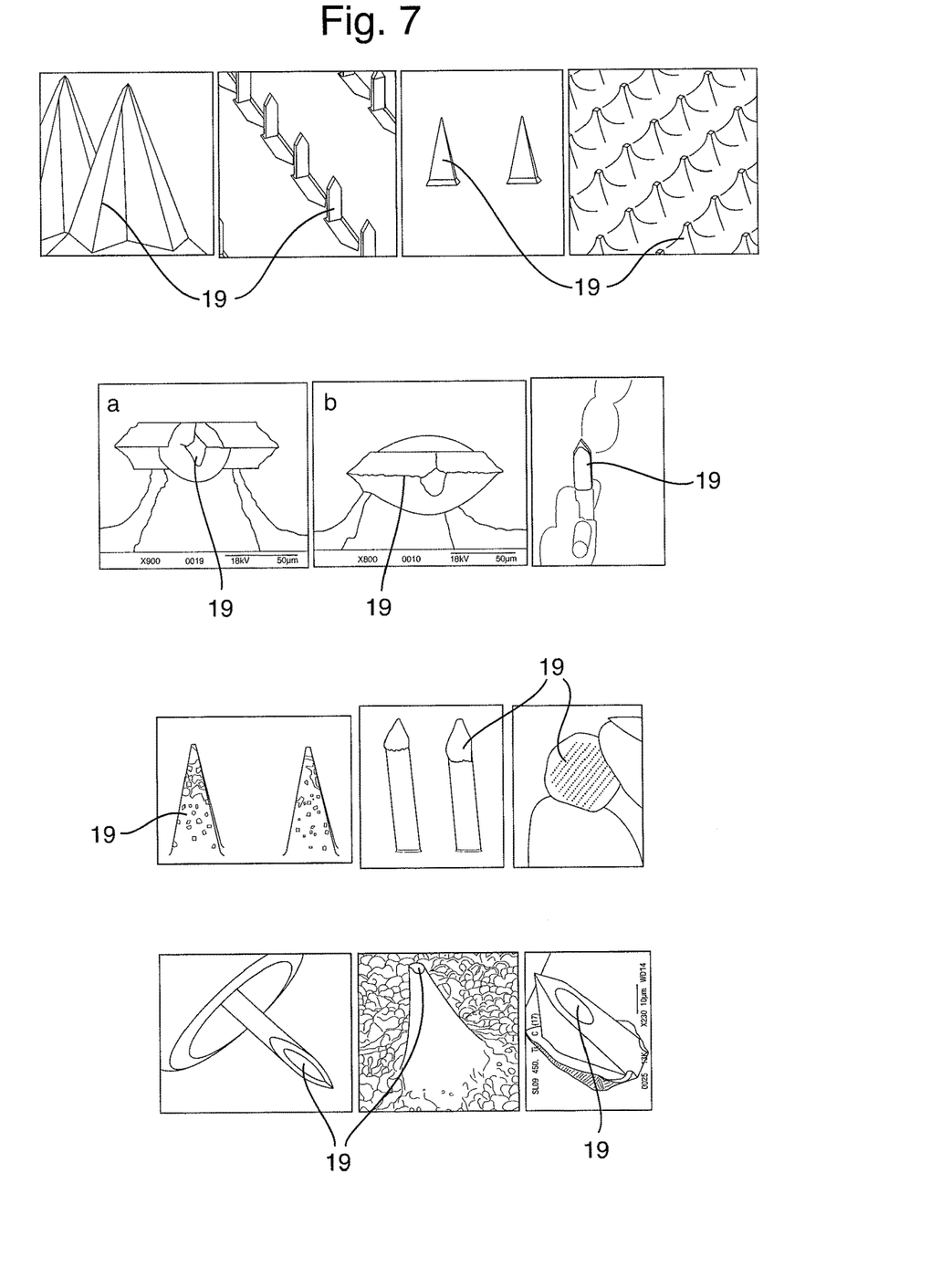
FIG. 7 illustrates examples of micro-needle arrangements that could be used in the drug administering portion.

FIG. 7 illustrates a non-exhaustive range of known micro-needle structures 19 that would be suitable for use in the drug administering portion 17. Arrays of hundreds of micro-needles per square centimetre of area may be used protruding a few hundred microns from a base substrate (e.g., they may be less than 500 μm high, more preferably less than 300 μm), either to pierce or to scrape microscopic holes in the skin's outer layer of stratum corneum. This is a layer which measures just 10-20 μm thick, but provides the skin's dominant barrier to percutaneous absorption. By piercing the skin, transdermal permeability is increased by as much as four orders of magnitude. In addition the transmission of the antigen and other components through a large number of points across the patient's skin also assists the take up of these components.

Thus in some examples, solid micro-needles 19 may be used that are prepared with dry antigen coatings applied onto a metal (or other material) micro-needle shaft.

Micro-needles may also be prepared completely out of polymer which also contain the antigen and/or photosensitising agent and/or adjuvant, most preferably an antigen and photosensitising agent. These can be made strong enough to insert into the skin. By using polymers that safely degrade or dissolve in the skin, micro-needles can be inserted into the skin and left in place for a few minutes (or longer if desired), after which the needles and their antigen payload have dissolved in the skin and only the device backing remains to be discarded. Transparent micro-needles, which do not dissolve, can also act as light-guides to guide light from the light source into the tissue of the patient.

Hollow micro-needles can also be used, which enable a liquid formulation to flow through the micro-needles and into the skin. Hypodermic needles measuring 1.0 to 1.5 mm in length skin, offering a penetration depth of up to 1.5 mm, are also appropriate for intradermal delivery irrespective of gender, age, ethnicity or body mass index. A disadvantage of such hollow micro-needles is that they need to store the liquid drug in a reservoir (often with an added complication of having to store the components separately) and an injection device is required to pump the drug through the bore of the micro-needles into the skin of the patient.

The most preferred system is where the micro-needles 19 are made of solid antigen (and photosensitising agent) and are intended to remain in place in the patient and dissolve during the activation cycle. The micro-needles 19 may be protected prior to use, for example, with a foil or film protective membrane that is removed prior to use and can keep the antigen and other components sterile. This foil or film may also uncover the adhesive patch(es) where present.

The micro-needles 19 may be of all the same depth or may be of different depths, for example, where different types of cell are being targeted. The patch may also comprise more than one type of micro-needle 19. For example, one type might comprise an antigen and another comprise a photosensitising agent. These might be different heights and/or comprise different coatings or substrate materials, e.g., in order to stagger the release of the antigen(s) and photosensitising agent(s) into the patient. In general the photosensitising agent will pass more quickly to the target cells than the antigen, and therefore it is preferable to provide some means to delay the release or slow the movement of the antigen. For example, the antigen and/or photosensitising agent may be encapsulated within nanoparticles that are coated on micro-needles or are part of the micro-needle composition and embedded within the dissolvable polymer micro-needles. Similarly an adjuvant may be provided that is encapsulated within nanoparticles.

The patch of micro-needles 19 may pierce the skin through the patient pressing the housing 2. In other embodiments, pressing the button 10 may deploy the micro-needles 19 into the patient's skin, either mechanically through the pressure applied to the button 10 displacing the micro-needles 19 within the housing and into the patient, or electronically through the button 10 activating an electronic circuit to deploy the micro-needles 19 through an electro-mechanical device. Pressing the button 10 preferably also initiates the activation cycle within a control system of the device 1.

A mechanism may be provided on the device 1 to indicate when sufficient pressure has been applied to properly deploy the micro-needles. For example, the button 10 might provide some feedback in the form of a noise or a movement that the person can feel (e.g., a click) to indicate that it has been pressed hard enough to deploy the micro-needles 19, and may also provide a clutch mechanism to prevent too much pressure being applied. In another embodiment, the device 1 may be loaded into an applicator that applies a pre-set amount of force as the device 1 is being fitted to the patient, for example, by preloading an ejector spring within the applicator that fires the device 1 onto the patient's skin.

The housing 2 also comprises a control system to control the operation of the light source, particularly once the activation cycle has been initiated. The control system is preferably a programmable controller that is configured to vary the output of the light source with respect to time in accordance with a pre-configured output sequence. The output sequence includes an initial stage where the output of the light source is set to be zero or generally below an intensity that can activate light-induced rupture of endocytic vesicles. This is to allow time for the photosensitising agent, and in particular the antigen, to reach the target cells before they are properly illuminated. The output sequence also includes a later stage where the output of the light source is set to be at an intensity above that which can activate light-induced rupture of the endocytic vesicles. This is in order to effect the light-induced delivery of the administered antigen in the vesicles to the target cells.

FIGS. 8a to 8d illustrate four exemplary output sequences for the light source during the activation cycle, showing intensity of output (I) with respect to time (t).

Figure 8A:
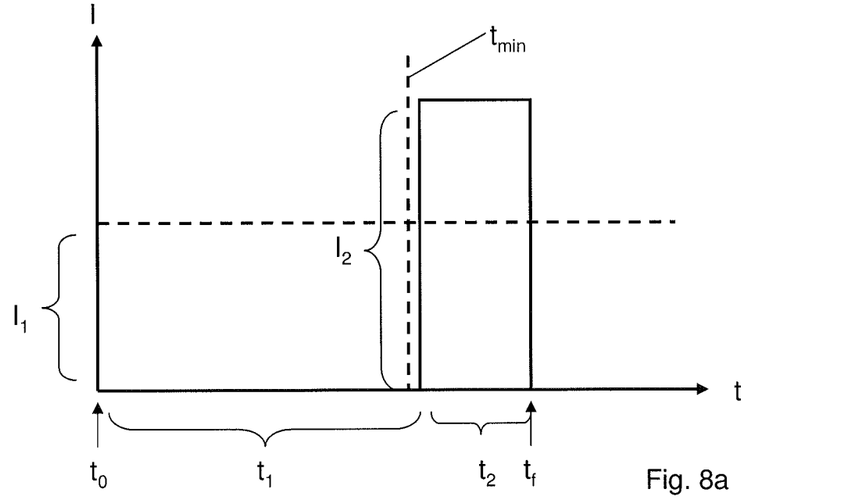
FIGS. 8a to 8d illustrate examples of output sequences that could be followed by the control system in the operation of the light source.

In FIG. 8a, $t_0$ is the initiation of the activation cycle, which in this case is the point where the antigen and/or photosensitising agent has/have been administered. These are preferably administered at the same time, e.g., through deploying micro-needles comprising both components, but could be administered at different times during the activation cycle with $t_0$ representing the first component, or the activation cycle could be initiated through an action causing deployment of the last component.

The time $t_{min}$ is the minimum period of time required for the antigen and photosensitising agent to reach the target cells and to be taken up into endocytic vesicles (the antigen within the vesicle and the photosensitising agent in the endosome membrane). It is preferably at least one hour, more preferably three hours, or even six hours. In many instances it can be twelve hours, twenty-four hours, or longer. In one example it is about 18 hours (±2 hours). In the output sequence for the light source of FIG. 8a, there is a corresponding initial stage $t_1$ equal to or greater than $t_{min}$, where there is no output from the light source. The light may be shielded by shutters during this time or, more preferably, the light source is switched off. Once the time $t_{min}$ has elapsed, light from the light source illuminates the region of the patient's skin where the antigen has been administered. The output of the light exceeds an intensity $I_1$ that can activate light-induced rupture of the endocytic vesicles, i.e., it exceeds a threshold light dose and/or irradiance that causes an oxidising reaction in the photosensitising agent to rupture the membrane to release the antigen into the cell cytosol. In the example shown, the light is at an intensity level $I_2$ for a period $t_2$, where $I_2$ is greater than the theoretical value $I_1$, possibly 10% greater than $I_1$, more preferably greater than 15%, in order to avoid edge effects and ensure activation over the complete area. As an example, the illumination time might be anything up to 15 hours, say 10 to 12 hours, or might be quite short, for example, between 5 to 30 minutes, or could be anywhere between these extremes.

The control system may be pre-configured to wait for a set period of time corresponding to $t_{min}$ or a short period thereafter before activating a circuit that switches on the light source for a pre-set period of time corresponding to $t_2$. At the end of the activation cycle $t_f$, the output of the light source is returned to zero, e.g., by switching off the light source.

Figure 8B:
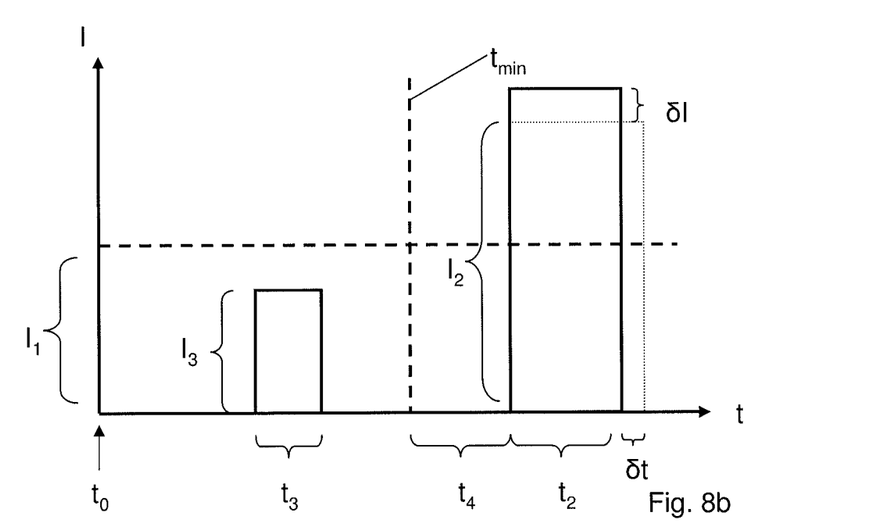

In FIG. 8b, in the period between $t_0$ and $t_{min}$, the output sequence is pre-configured to emit a pulse of light at an intensity $I_3$ (light dose and/or irradiance which is less than the intensity $I_1$) for a period $t_3$. A pre-activation illumination of the antigen, particularly where an adjuvant is used, might provide a beneficial response in the patient. Too much light intensity, however, during this initial period $t_1$ can be detrimental to the operation of the photosensitising agent and the delivery of the antigen.

In the output sequence of FIG. 8b, there is a further period of delay $t_4$ prior to emitting the pulse of light that will induce the rupture of the endocytic vesicles, in this example the pulse which is at an intensity of $I_2+\delta I$ for a period $t_2$. During this period $t_4$, the device 1 might monitor the extent of the take up of photosensitising agent, for example, through monitoring the change in fluorescence of the photosensitising agent or a marker, or it might monitor some other indicator of the process and delay the activation pulse accordingly beyond $t_{min}$ for a time $t_4$. The device 1 may also measure the light absorption characteristics of the patient's skin, or respond to an input on the device indicating the skin colour, and adjust the intensity of the output accordingly, in this case increasing the activating pulse to an intensity of $I_2+\delta I$ ($\delta I$ indicating an adjustment to the pre-configured intensity level). In another example, the period of the activating pulse might be increased from $t_2$ to $t_2+\delta t$ ($\delta t$ indicating an adjustment to the pre-configured pulse duration), for example, in the case of dark skin.

Figure 8C:
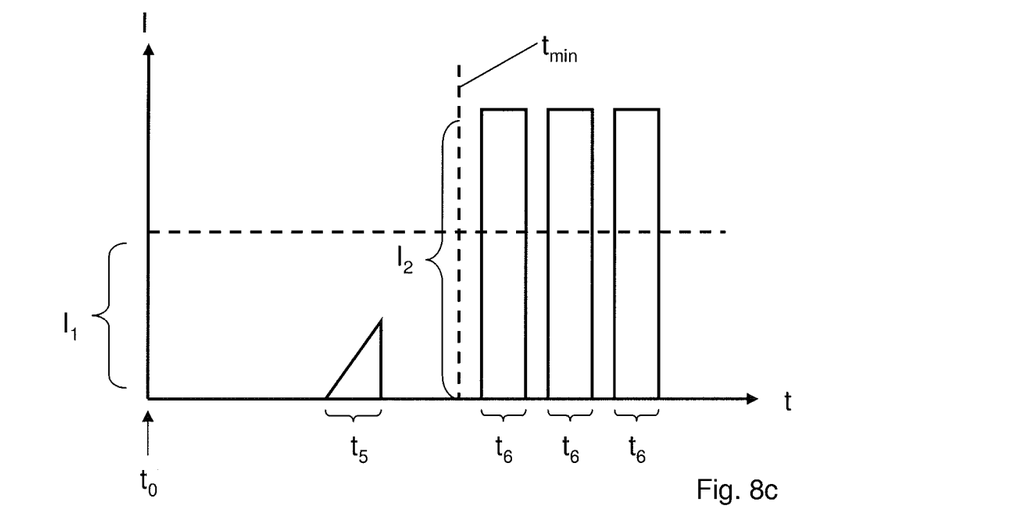

In the output sequence of FIG. 8c, there is an initial pre-activation pulse for a period of $t_5$ prior to time $t_{min}$. Rather than a square output profile, this pulse is a ramped profile where the intensity of the light increases steadily for the period $t_5$. This initial pre-activation pulse could, of course, be a different profile or comprise multiple pulses as desired for optimal clinical response to the antigen. After time $t_{min}$, there are shown three pulses of intensity $I_2$ each for a period of $t_6$, where $t_6$ is less than $t_2$. The pulses could, of course, be of different durations, amplitudes or profiles, or there could be different dwell times between the pulses, depending on the photosensitising agent used and the target cells.

Figure 8D:
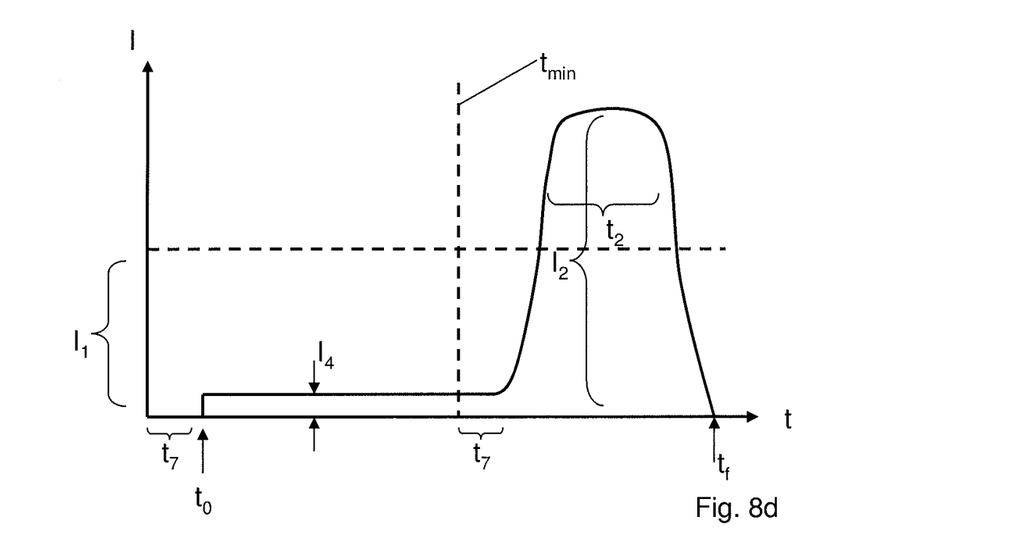

FIG. 8d shows a further example where the light source emits at a low intensity (light dose and/or irradiance) during the initial stage (intensity $I_4$) which is a substantial way below the intensity $I_1$, the light being emitted from a start point $t_0$ after a period $t_7$ where no light is emitted. This illumination of intensity $I_4$ may be to provide a visual cue to the patient that the device is operating and needs to be kept in place over where the antigen and photosensitising agent have been administered. The period $t_7$ may be, for example, to allow time to apply the antigen and the photosensitising agent as an ointment to the patient, as well as possibly to allow for the fitting of the device 1. The activation peak after $t_{min}$, in this case $t_{min}+t_7$, comprises a rounded profile which overall provides an intensity of $I_2$ for a period of $t_2$ prior to the finish at $t_f$.

These four output sequences are exemplary and are not intended to be exhaustive of all the possibilities. Features of the output sequences may be combined and exchanged with one another even if not expressly mentioned. Similarly the timings or profiles of the pulses may be adjusted as desired to optimise the patient's response to the antigen.

The device 1 also has a power supply (not visible in the figures) to power the light source and the control system, and is preferably in the form of an internal battery. As the battery can be one of the heaviest components, it could also be contained within a separate housing and coupled to the device 1 with an electrical lead. In one example, a strip of insulating material is provided between an electrical contact of the power supply to prolong the battery life, which is removed during fitting of the device 1. The connecting up of the power supply, e.g. by removing a circuit break or through plugging a lead from a power supply into the device, etc., can also be used to initiate the activation cycle.

The device 1 is for external use only. It is preferably constructed as a single use item, i.e., it is intended to be used to deliver the antigen and then thrown away. By having a separable power supply, this can facilitate appropriate disposal of the parts. It may also be possible to recycle part or the whole of the device, e.g., for re-use on a different patient.

The invention claimed is:

1. A device for activating light-induced rupture of endocytic vesicles in target cells of a patient so as to effect delivery of an administered antigen to cytosol in the target cells, the device being adapted to be worn by a patient over a region of the patient's skin where an antigen and a photosensitising agent have been or are to be administered, wherein the device comprises:
 a rear surface that is configured to be worn against the patient's skin;
 a retaining part for retaining the device in place over the region of the patient's skin during an activation cycle;
 a light source arranged to illuminate the region of the patient's skin from the rear surface of the device;
 a control system to control the operation of the light source after initiation of the activation cycle; and
 a power supply to power the light source and the control system,
 wherein the control system is configured to vary the output of the light source with respect to time in accordance with a pre-configured output sequence, wherein the output sequence includes an initial stage of at least six hours where the output of the light source is set to be zero or generally below that which could deliver a light dose that can activate light-induced rupture of endocytic vesicles to allow time for the antigen and photosensitising agent to reach the target cells, and a later stage where the output of the light source is set to deliver a light dose to activate light-induced rupture of the endocytic vesicles for effecting the delivery of the administered antigen to the cytosol of the target cells, wherein the light dose is at least 0.05 J/cm$^2$ and is delivered over 5 minutes to 15 hours at an intensity of 0.5 mW/cm$^2$ or less.

2. A device as claimed in claim 1, wherein the device is provided with a drug administering portion for administering the antigen and/or photosensitising agent, the drug administering portion comprising a store of antigen and/or photosensitising agent for administering to the patient, and preferably also a store of adjuvant.

3. A device as claimed in claim 2, wherein the drug administering portion comprises a micro-needle or a patch of micro-needles.

4. A device as claimed in claim 3, wherein the micro-needles comprise a polymer that is intended to dissolve in the patient, within which is provided the antigen and/or photosensitising agent.

5. A device as claimed in claim 3, wherein the micro-needles comprise a coating comprising the antigen and/or photosensitising agent.

6. A device as claimed in claim 5, wherein the antigen and/or photosensitising agent is encapsulated within particles in or on the micro-needles.

7. A device as claimed in claim 4, wherein the antigen and/or photosensitising agent is encapsulated within particles in or on the micro-needles.

8. A device as claimed in claim 3, wherein the micro-needles comprise hollow projections through which the antigen and/or photosensitising agent is administered.

9. A device as claimed in claim 1, wherein the light source comprises one or more light emitting devices which are arranged to illuminate the patient's skin directly or via a light guide, preferably in the form of micro-needles.

10. A device as claimed in claim 1, wherein the retaining part comprises an adhesive patch and/or a strap, web or sleeve for fitting around a limb of the patient.

11. A device as claimed in claim 1, wherein the device is configured to be worn on the patient's arm, preferably an upper region of the arm.

12. A device as claimed in claim 1, wherein the control system is configured to deliver an output sequence from the light source comprising a plurality of pulses of light.

13. A device as claimed in claim 1, wherein the device comprises a sealing layer that is removed prior to use.

14. A device as claimed in claim 1, wherein a sensor is provided to monitor the fluorescence of a component during the activation cycle.

15. A method of activating light-induced rupture of endocytic vesicles in target cells of a patient so as to effect delivery of an administered antigen to cytosol in the target cells, the method comprising:
 administering an antigen and a photosensitising agent to a region of the patient's skin;
 wearing a device as claimed in any preceding claim for activating the light-induced rupture of endocytic vesicles in the target cells;
 initiating an activation cycle on the device for the light-induced rupture of the endocytic vesicles;
 during the activation cycle, illuminating the region of the patient's skin from the rear surface of the device in accordance with a pre-configured output sequence controlled by a control system of the device, wherein the output sequence includes an initial stage of at least six hours where the output of the light source is set to be zero or generally below that which could deliver a light dose that can activate light-induced rupture of endocytic vesicles to allow time for the antigen and photosensitising agent to reach the target cells, and a later stage where the output of the light source is set to deliver a light dose to activate light-induced rupture of the endocytic vesicles for effecting the delivery of the administered antigen to the cytosol in the target cells, wherein the light dose is at least 0.05 J/cm$^2$ and is delivered over 5 minutes to 15 hours at an intensity of 0.5 mW/cm$^2$ or less.

* * * * *